United States Patent [19]

Lin

[11] Patent Number: 4,667,053
[45] Date of Patent: May 19, 1987

[54] PROCESS FOR OXIDATIVE CARBONYLATION USING A CATALYST HAVING A NOVEL SUPPORT

[75] Inventor: Jiang-Jen Lin, Round Rock, Tex.

[73] Assignee: Texaco Inc., White Plains, N.Y.

[21] Appl. No.: 880,394

[22] Filed: Jun. 30, 1986

[51] Int. Cl.$^4$ ............................................. C07C 67/38
[52] U.S. Cl. .................................. 560/204; 502/102; 502/230; 502/402; 560/190
[58] Field of Search ................ 560/204, 190; 502/102, 502/230, 402

[56] References Cited

U.S. PATENT DOCUMENTS 4,281,174 7/1981 Current .............................. 560/204
4,552,976 11/1985 Lin et al. ............................ 560/204

Primary Examiner—Natalie Trousof
Assistant Examiner—Vera C. Clarke
Attorney, Agent, or Firm—Jack H. Park; Kenneth R. Priem; Cynthia L. Kendrick

[57] ABSTRACT

This invention relates to the carbonylation of olefins. More particularly it involves the carbonylation of an α-olefins such as ethylene to form diesters, such as, for example, dimethyl succinate, 3-methoxypropionate and dimethylcarbonate by a process comprising reacting said olefin with carbon monoxide, oxygen and an alkanol in the presence of a heterogeneous palladium/copper catalyst, on a polymer support.

9 Claims, No Drawings

PROCESS FOR OXIDATIVE CARBONYLATION USING A CATALYST HAVING A NOVEL SUPPORT

FIELD OF THE INVENTION

This invention relates to the carbonylation of simple olefins. More particularly this invention relates to a heterogenous palladium/copper catalyst on a polymer support for the carbonylation of simple olefins such as ethylene to diesters.

BACKGROUND OF THE INVENTION

The addition of carbon monoxide to olefins (carbonylation) has long been considered in the art to be a highly attractive route to a number of commercially valuable chemical products. It is known in the art to prepare unsaturated aliphatic carboxylic acids and their esters by the catalytic oxidative carbonylation of an olefin. More particularly, it is known to synthesize aliphatic carboxylic acids and their esters by reacting carbon monoxide, oxygen and an olefin such as octene or propylene under elevated temperature and pressure conditions in the presence of various catalysts, often in the presence of dehydrating agents. One useful type of ester is an alkyl succinate which is a precursor for alkyl succinic anhydrides or diols. The related polyakenyl succinic anhydride is used for lubricating oil additives and for polyester resins.

Some of the early patents in the field, such as U.S. Pat. Nos. 3,397,226, 3,397,225, 3,481,845 and 3,755,421, demonstrate the use of catalysts comprising a platinum group metal salt or chelate and a multivalent heavy metal salt which functions as a redox agent for the oxidative carbonylation of hydrocarbon olefins to produce esters of unsaturated carboxylic acids, esters and dicarboxylic acids and esters of beta-alkoxy-substituted carboxylic acids.

In another process which is disclosed in *J. Org. Chem.* 1979, 44(20), 3474-82, methoxycarbonylation of a variety of olefins with methanol and carbon monoxide takes place in the presence of palladium, using stoichiometric amounts of copper(II) chloride as a reoxidant, and sodium butyrate as a buffer. Different aliphatic carboxylic acid diesters were formed in varying yields depending on the choice of diolefin and the carbon monoxide pressure. The reaction usually resulted in the addition of two carbomethoxy functions to the double bond.

In *J. Am. Chem. Soc.* 98, 1810 (1976), James and Stille provide much data on the yields of various esters using different cyclic and acyclic olefin reactants. They also discuss the effects of some of the cocatalysts, etc. used in many of these reactions and yields of products. Again palladium(II) chloride is employed as catalyst, and stoichiometric amounts of copper(II) chloride are used as the reoxidant. The effect of added base is also discussed.

A study reported in *J. Org. Chem.* 37 2034 (1972) discussed experiments which demonstrate that in a palladium redox system, optimum results are achieved by restricting both amounts of excess hydrogen ion and chloride ion.

U.S. Pat. No. 4,281,174 discloses a catalyst system for preparing dimethyl oxalates by the oxidative carbonylation of alcohol which involves the reaction of CO, air and alcohol. Dimethyl carbonate can also be produced with a similar Pd catalyst.

In many processes known in the art separation of the high boiling aliphatic carboxylic acid or ester product from the catalyst system can be difficult. A supported palladium/copper catalyst system which allowed for easier separation of product from catalyst by filtration would be efficient and attractive commercially. A further advance would comprise the selection of a suitable support for such a palladium/copper catalyst system which would improve both the productivity and the selectivity to the desired product or products.

In recent U.S. Pat. Nos. 4,552,976 and 4,554,374 the oxidative dicarbonylation of 1,3-butadiene and α-olefins using a heterogeneous palladium catalyst such as palladium on graphite has been demonstrated. The reaction rate and the product selectivity were affected by the type of supports for the palladium catalyst. However, a support comprising a copper catalyst in combination with a palladium catalyst for oxidative carbonylation has not yet been suggested in the art.

SUMMARY OF THE INVENTION

The present invention provides a process for the improved production of diester precursors of 1,4-butanediol and acrylic acid by the oxidative carbonylation of α-olefins with carbon monoxide and an alkanol in the presence of a catalyst comprising (1) palladium and copper on a polymer support or (2) mixed palladium on carbon and copper on a polymer support.

This invention demonstrates improved product selectivity, improved control over ratio of products and improvement in ease, efficiency and commercial attractiveness of means of separation of the product.

DESCRIPTION OF THE INVENTION

One or more objects of the present invention are accomplished by the process of the instant invention comprising reacting an α-olefin, methanol and 2,2-dimethoxypropane (a dehydrating agent) with carbon monoxide and oxygen over a heterogenous, supported, palladium/copper catalyst in a reaction vessel and subjecting the contents of the charged vessel to a carbon monoxide pressure and a temperature sufficient to effect the carbonylation reaction.

In accordance with the invention α-olefins of the formula:

wherein R is an alkyl or hydrogen, are converted by the palladium/copper catalyzed addition to said double bond of carbon monoxide, oxygen and an alkanol, to produce aliphatic dicarboxylic esters in which the double bonds have been transformed into a diester having the formula:

wherein R' is an alkyl group from an alkanol, such as a methyl group from methanol. The process comprises passing the α-olefin, carbon monoxide and oxygen together with an alkanol over a heterogenous supported palladium/copper catalyst wherein the support comprises a polymer. The reactants and catalyst components are charged to a reaction vessel and, in the absence of water, subjected to a carbon monoxide pressure and temperature for a sufficient period of time to effect the desired carbonylation reaction. In the specific use of the olefin ethylene, the carbonylation reaction can be represented by the following equation:

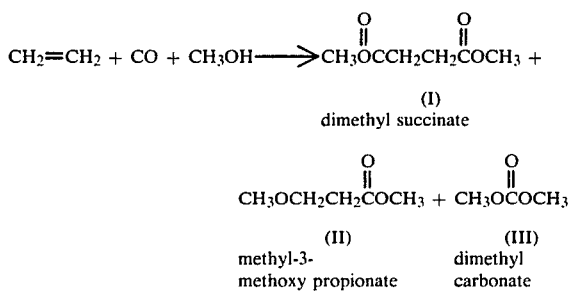

(I) dimethyl succinate (II) methyl-3-methoxy propionate (III) dimethyl carbonate Generally the reaction between the α-olefin, carbon monoxide, oxygen and alkanol may be carried out in an autoclave or other appropriate reactor. Although the order of addition of reactants and catalyst components may vary, a general procedure is to charge the supported palladium/copper catalyst, α-olefin, alkanol and optional dehydrating agent to an appropriate reactor, such as a stainless-steel, magnedrive reactor, then introduce the proper amount of carbon monoxide and oxygen and increase the pressure and temperature to a desired level for an appropriate period to produce the desired aliphatic dicarboxylic ester.

Olefins suitable for use in the present invention are simple olefins containing two to twelve atoms per molecule and having the general formula:

R—CH=CH$_2$ wherein R is hydrogen or a hydrocarbon radical.

Suitable olefins include ethylene, propylene, 1-butene, 1-pentene, 1-hexene, 1-heptene, 1-octene, 1-nonene, 1-decene, 1-undecene, 1-dodecene and the like. The preferred α-olefin for the practice of this invention is ethylene.

The alcohol coreactants used in these syntheses are aliphatic monohydric alkanols each containing one to twenty carbon atoms per molecule. Suitable aliphatic monohydric alkanols include methanol, ethanol, n-propanol, iso-propanol, tert-butanol, n-butanol, n-hexanol, n-decanol, n-dodecanol and the like. The preferred aliphatic monohydric alkanol coreactant is methanol.

As mentioned above a palladium/copper catalyst compound is employed in the process of the invention, which together with the particular support provides a catalyst system which demonstrates an increase in selectivity for carboxylic acid ester products and which allows for control over ratio of products and ease of separation, features which are commercially attractive and desired in the art. The palladium/copper catalyst is preferentially present in an embodiment wherein the palladium and copper are bonded to a polymer support. The polymer support can be a polyamine or a polyvinyl pyrrolidone. Suitable supports include any forms of poly(pyrrolidone) such as polyvinylpyrrolidone (molecular weight can be up to 360,000) for palladium and copper catalysts. Polyamine supports include Amberlyst ® A-21, poly(2-vinylpyridine), and poly(vinylpyridine-Co-styrene), for copper catalyst. The preferred support is polyvinylpyrrolidone or Amberlyst ® A-21. The catalyst which is supported can comprise palladium and copper on a polymer or it can comprise palladium on carbon and copper on a polymer in combination. The latter is demonstrated in Examples 6–8. The palladium/copper concentration on the support may vary from 0.1 wt% to 20 wt%. This is the range normally employed, with the preferred range being 0.5 wt% to 5.0 wt%.

The polymer support may be in the form of an ion-exchange resin. In the embodiment where the copper is supported on a polymer and the palladium is supported on carbon, the carbon can be in the form of powders, pellets, spheres, shapes and extrudates. They should be of suitable porosity such that they may be employed in fixed bed ratios.

The palladium-containing precursor compound to be dispersed upon the solid support or carbon may be impregnated on said supports in the form of a bivalent palladium-containing salt, possibly as the salt of a carboxylic acid such as palladium acetate, palladium propionate, or as palladium acetylacetonate, palladium nitrate and the like. Alternately it can be added in the form of a palladium halide, such as palladium(II) chloride.

Generally, said palladium-containing catalyst system is prepared by first dissolving or slurrying the selected palladium salt, halide, etc., e.g. palladium(II) chloride, with a suitable solvent system and subsequently impregnating the selected polymer support or carrier with the palladium-containing mixture. These solutions or slurries may be poured onto the carrier, or the solid carrier may be immersed in an excess of the liquid solution or slurries, with the excess being subsequently removed.

The copper-containing catalyst is prepared by first dissolving or slurrying the selected copper-containing catalyst in the form of a salt of copper such as a halide, sulfate, trifluoroacetate, nitrate, naphthalenate, hex-3-endioates or acetate. Copper salts which work include, but are not limited to copper(II) chloride, copper(II) bromide, copper(II) sulfate, cuprous chloride hydrate, copper(II) trifluoroacetate, copper(II) acetate, copper(II) triflate, copper(II) fluorosulfonate, copper(I) chloride and copper(I) sulfate.

The preferred compound is copper(II) chloride.

The impregnated support is then maintained at a temperature sufficient to volatize the solvent component, e.g. at a temperature between 100° C. and 500° C., to permit drying of the composite solid catalyst. A vacuum may also be applied to the catalyst in order to volatize the solvent, although use of a vacuum is not essential. During this stage of the process the volatile solvent evaporates from the solid catalytic products, and the ruthenium component remains on the support.

The solvent which may be used to dissolve the palladium-containing compound prior to impregnation onto the support should be a liquid of relatively low boiling point such as, for example, about 150° C. or less. A preferable group of solvents include mineral acid solutions such as hydrochloric acid and nitric acid, carboxylic acids such as acetic acid and propionic acid, halogenated solvents like chloroform and carbon tetrachloride, ketones such as acetone and methyl isobutyl ketone, alcohols such as methanol, iso-propanol and tert-butanol, aromatics such as benzene, toluene and xylene, as well as certain heterocyclic solvents like pyridine and N-methylpyrrolidone. The choice of solvent is dependent upon the nature of the palladium and copper-containing compounds to be used for impregnation.

Optionally a dehydrating agent may also be added to the reaction mixture in the practice of this invention. Suitable dehydrating agents that may be used during the preparation of said aliphatic carboxylic acid esters include certain acetals and ketals. These may include acetaldehyde dimethyl acetal, benzaldehyde dimethyl acetal and formaldehyde dimethyl acetal. Suitable ketals can be 2,2-dimethoxypropane, dimethoxymethane and the like. Said dehydrating agent may be used in a wide range of ratios compared with the quantity of aliphatic conjugated diene charged, but in the case of α-olefin carbonylation, preferably 1-2 moles, or more, of dehydrating agent, such as 2,2-dimethoxypropane, are employed per mole of α-olefins charged.

The process of the present invention can be suitably performed by introducing the oxygen, carbon monoxide and alcohol at a desired pressure into contact with the olefin, preferably ethylene, optional dehydrating agent and the supported palladium/copper catalyst and heating to the desired temperature.

In general a carbon monoxide pressure of about 50 psig to about 5000 psig partial pressure and preferably from about 500 psig to about 2500 psig is employed. At least stoichiometric quantities of carbon monoxide are generally employed. However, an excess of carbon monoxide may be employed, for example, particularly in continuous processes. Where a large excess of, or high carbon monoxide requirements are generally utilized, a suitable recycle of the unreacted carbon monoxide may be employed.

The partial pressure of oxygen is generally selected so that the molar ratio of carbon monoxide to oxygen is in the range of 1:1 to 100:1. A carbon monoxide to oxygen ratio in the range of 5:1 to 20:1 has been employed in this work for the synthesis of succinate from α-olefins, and is considered to be the preferred range.

The reaction will proceed at temperatures above 25° C. It is generally preferred to operate the process at temperatures in the range of 80° C. to 150° C. to obtain a convenient rate of reaction with the particular olefin.

The reaction time is generally dependent upon the olefin being reacted, temperature, pressure and on the amount and type of catalyst support and dehydrating agent being employed. Reaction time will vary dependent on whether the process is continuous or batch and may vary from one to 15 hours. Reaction time for α-olefins is generally about two hours.

The quantity of palladium/copper catalyst employed in the instant invention is not critical and may vary over a wide range. In general, the carbonylation process is desirably conducted in the presence of a catalytically effective quantity of the active palladium/copper species which gives the desired ester products in reasonable yields.

The reaction proceeds when employing concentrations of palladium/copper-containing compound of between 0.01 wt% and 50 wt%, with the preferred range being 0.1 wt% to 1 wt% and optimally about 0.5 wt%. Higher concentrations of palladium/copper-containing compound may be used to the extent of 50 wt%.

The ratio of supported palladium-containing compound to copper-containing compound within the concentration of total catalyst on the support is not critical. Good results are obtained using a weight ratio of Pd:Cu of about 1:100 to 1:1. The presence of lithium-containing cocatalyst is not critical and is optionally employed in the instant invention. If lithium is used, the concentration of lithium-containing compound at the range of 0.0001 wt% to 1.0 wt% is preferred.

In reacting an α-olefin, carbon monoxide, oxygen and an alcohol in the presence of the catalyst to form a diester, whether accomplished in continuous operations or batch experiments, the carbon monoxide may also be used in conjunction with up to 50% by volume of one or more other gases. These other gases may include one or more inert gases such as nitrogen, argon, neon and the like, or they may include gases that may, or may not, undergo reaction under CO carbonylation conditions such as carbon dioxide, hydrogen, hydrocarbons such as methane, ethane, propane and the like, ethers such as dimethyl ether, methylethyl ether and diethyl ether, and acid esters such as methyl acetate.

The α-olefin carbonylation process disclosed herein leads to the formation of two classes of products. The primary product is a dialkyl ester such as dimethyl succinate or methyl 3-methoxypropionate. By-products include dimethyl carbonate and β-alkoxy-carboxylate.

The benefits of the improved α-olefin carbonylation process using the supported palladium/copper catalyst and optional dehydrating agent are:

(a) increased productivity and selectivity of alkyl succinate product;

(b) ease of separation of said alkyl succinate from the palladium catalyst component;

(c) production of the useful by-product dimethyl carbonate from methanol and CO.

Generally, operating conditions can be adjusted to optimize the formation of any desired aliphatic carboxylic diester product, and said materials may be recovered by methods well known in the art, such as filtration, distillation, fractionation, extraction and the like.

In the process of this invention it has been found that selectivity to the various products is dependent upon the type of polymer support used. When the Amberlyst ® A-21 polyamine ion exchange resin was used the selectivity for dimethyl succinate was 86%. When the polyvinyl pyrrolidone catalyst was used the selectivity to dimethyl succinate was 53% and the selectivity to methyl 3-methoxypropionate was 41%.

The process of this invention can be conducted in a batch, semi-continuous or continuous fashion. The solid catalyst may be employed as a fixed bed. The reactor may consist of a series of catalyst beds or the catalyst may be placed in tubes with a heat exchange medium around the tubes. So as to provide certain operating advantages, the metal content of the catalyst may be varied through the reactor bed, and the reactants may be passed up-flow or down-flow through the reactor.

To ensure maximum yields of desirable products, contact between the liquid reaction mix and any iron-rich metal surfaces should be limited wherever possible during the carbonylation step. One means by which this contact can be minimized is by carrying out the olefin carbonylation reaction in a glass-lined reactor. A second, alternative method is to have the carbonylation reactor lined with some other inert materials, such as a silver lining, prior to effecting the diene carbonylation. Further alternatives include the use of titanium-lined pressure reactors, tantalum-lined reactors, and reactors having Hastelloy alloy or copper-nickel alloy surfaces.

The products of this improved catalyst system have been identified by one or more of the following analytical procedures, viz, gas-liquid phase chromatography (glc), infrared (ir) mass spectrometry, nuclear magnetic resonance (nmr) and elemental analysis, or a combination of these techniques. All temperatures are in degrees centigrade and all pressures in pounds per square inch gauge (psi).

Having described the inventive process, the following examples are submitted to supply specific and illustrative embodiments.

It is to be understood these examples are illustrative and the invention is not to be limited thereby:

The following equation describes the basic reaction described in Examples I–VIII.

EXAMPLE 1

Preparation of Polyvinylpyrrolidone-Supported Palladium-Catalyst

A mixture of palladium chloride (1.75 g), cupric chloride (13.5 g) and polyvinylpyrrolidone (22.2 g) in ca. 500 ml methanol was stirred at room temperature overnight. The solid material was obtained by filtration and washed thoroughly with additional methanol. The solid material was dried at 50° C. under vacuum for 2 hours. The resulting solid (27.2 g), brown in color, was analyzed. Metal content showed 3.83% palladium and 2.28% copper.

EXAMPLE 2

A 183 ml glass-lined reactor was charged with palladium/copper catalyst (3.0 g, prepared from Example 1), lithium chloride (0.084 g), methanol (0.5 g), 2,2-dimethoxypropane (15.0 g) and ca. 9.0 g ethylene. The reactor was pressured with carbon monoxide (500 psi) and oxygen (200 psi) and then was heated to 100° C. At this temperature, the pressure of 1200 psi was recorded. The system was pressured with carbon monoxide to 2000 psi and held for 2 hours reaction time. During the reaction process, 350 psi of pressure uptake was observed. The reactor was allowed to cool to room temperature and excess gas was vented. The resulting liquid product and solid catalyst (ca. 22.5 g) was obtained. The glc analysis of liquid materials showed 17% dimethyl succinate and 13% methyl 3-methoxypropionate in solution. The product selectivity was estimated to be 53% for dimethyl succinate, 41% for methyl 3-methoxypropionate, 0% for dimethyl carbonate and ca. 6% for dimethyl oxalate.

EXAMPLE 3

The experimental procedures of Example 2 were repeated, except a palladium/copper catalyst (2.0 g, prepared from Example 1), methanol (0.5 g), 2,2-dimethoxypropane (15.0 g) and ethylene (ca. 8.0 g) was charged into the glass-lined reactor. There was no lithium chloride charged. The reactor was sealed and 200 psi of oxygen, 500 psi of carbon monoxide was initially charged. The system was heated to 100° C. and pressure was raised by additional carbon monoxide to 2000 psi. During the reaction process, 350 psi of pressure uptake was noted. After 2 hours reaction time, the reactor was cooled to room temperature and excess gas was vented. The resulting material (21.8 g) was recovered. The glc analysis of liquid products showed 13% of dimethyl succinate in the solution. The product selectivity was calculated to be 55% for dimethyl succinate, 14% for methyl 3-methoxypropionate, 11% for dimethyl carbonate and unknowns.

EXAMPLE 4

The reaction mixture obtained from the previous run was filtered, the solid catalyst was recovered and dried under high vacuum at 60° C. The resulting grey-colored solid (2.0 g) was recharged into the reactor with methanol (0.5 g), 2,2-dimethoxypropane (15.0 g) and ethylene (9.5 g). Similar reaction conditions (2000 psi $CO/H_2 = 10:1$ mixture, 100° C. and 2 hours) were applied. The product solution (19.2 g) was analyzed by glc and showed 13.0% of dimethyl succinate in the solution. The calculated product selectivities are 68% for dimethyl succinate and 18% for methyl 3-methoxypropionate. The reuse of the solid catalyst (with a slightly improved selectivity) was demonstrated.

EXAMPLE 5

The Preparation of Polyamine Supported Copper Catalyst

A mixture of cupric chloride (20.0 g), methanol (200 ml) and Amberlyst® A-21 ion-exchange resin (from Aldrich Chemical Co.) was stirred at room temperature for two days. The solid material was recovered by filtration. The material contained ca. 1.65% copper.

EXAMPLE 6

Procedures similar to that of Example 2 were used. The autoclave was charged with Pd on graphite (1%) (Alfa Inorganic) (1.0 g), copper-polymer-supported catalyst (3.0 g) from Example 5), methanol (0.5 g), 2,2-dimethoxypropane (15 g) and ethylene (10 g). The reaction conditions of 200 psi $O_2$ and 2000 psi CO, 100° C. and 2 hours were used. The analysis showed 23% dimethyl succinate in solution (24.7 g). The selectivities were calculated to be ca. 43% for dimethyl succinate and 15% for methyl 3-methoxypropionate.

EXAMPLE 7

The procedure of Example 2 was used, except the mixture of Pd on graphite 1% (1.0 g), supported copper solid catalyst from Example 5 (3.0 g), 2,2-dimethoxypropane (15 g) and ethylene (ca. 10) was charged. The reaction conditions were 80° C., 200 psi $O_2$ and 2000 psi CO for 2 hours. The recovered material (21.0 g) showed ca. 6% dimethyl succinate in solution. The lower reaction temperature at 80° C. demonstrated only low activity.

EXAMPLE 8

Using similar reaction procedures, the mixture of palladium on graphite (1.0 g), copper on Amberlyst® A-21 (from Example 5) (3.0 g), methanol (0.5 g), 2,2-dimethoxypropane (15 g) and ethylene (ca. 17 g) was charged. At the conditions of 100° C., 100 psi of $O_2$, 2000 psi CO and 2 hours, the recovered material (23.8 g) showed 25% of dimethyl succinate and 18% of dimethyl carbonate. The selectivity to dimethyl succinate based on ethylene-derived product was ca. 86%.

The selectivity and productivity from various polymer-supported catalysts were demonstrated and it was found that:

1. Higher selectivity for dimethyl succinate was found using the polyamine support.
2. There was good combined selectivity foYboth dimethyl succinate and methyl 3-methoxypropionate using a polyvinylpyrrolidone catalyst support.
3. Dimethyl carbonate is the major by-product in most cases.

What is claimed is:

1. A process for oxidative carbonylation of an alpha olefin containing 2 to 20 carbon atoms per molecule by reaction with carbon monoxide and oxygen in the presence of an alkanol coreactant containing 1 to 20 carbon atoms per molecule to form an aliphatic dicarboxylic ester having the formula:

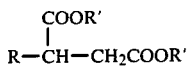

wherein R' is an alkyl group from said alkanol coreactant, said process being conducted in the presence of a heterogeneous, solid supported catalyst wherein the catalyst is selected from the group consisting of (1) palladium and copper and (2) mixed palladium on carbon and copper on a polymer support at a temperature of at least 50° C. and a pressure of at least 500 psi wherein the support is a polymer selected from the group consisting of pyrrolidones and polyamines, and the type of polymer used for the support affects selectivities for esters.

2. A process according to claim 1 wherein the α-olefin is ethylene, the alkanol is coreactant methanol, the heterogeneous catalyst is palladium and copper and the polymer is selected from the group consisting of polyamine and polyvinylpyrrolidone.

3. A process according to claim 2 wherein the temperature is from 80° C. to 150° C.

4. A process according to claim 2 wherein the carbon monoxide pressure is from 500 psi to 2500 psi.

5. A process according to claim 2 wherein the carbon monoxide to oxygen ratio is from 5:1 to 20:1.

6. A process according to claim 1 wherein the support for the palladium and copper catalyst is a solid form of polyamine.

7. A process according to claim 1 wherein the support for the palladium catalyst is a solid form of polyvinylpyrrolidone.

8. A process according to claim 1 wherein the palladium and copper-containing catalyst is deposited on said support in a concentration range of 0.1 to 20 wt%.

9. A process according to claim 2 wherein a copper catalyst is supported on a solid support selected from the group consisting of a polyvinylpyrrolidone and polyamine in combination with a palladium catalyst supported on carbon.

* * * * *